United States Patent [19]
Berg

[11] Patent Number: 4,695,350
[45] Date of Patent: * Sep. 22, 1987

[54] SEPARATION OF N-HEXYL ACETATE FROM N-HEXYL ALCOHOL BY EXTRACTIVE DISTILLATION

[76] Inventor: Lloyd Berg, 1314 S. Third Ave., Bozeman, Mont. 59715

[*] Notice: The portion of the term of this patent subsequent to Jun. 25, 2002 has been disclaimed.

[21] Appl. No.: 822,604

[22] Filed: Jan. 27, 1986

[51] Int. Cl.$^4$ .......................... B01D 3/40; C07C 67/48
[52] U.S. Cl. ........................................ 203/51; 203/56; 203/57; 203/60; 203/64; 560/248
[58] Field of Search .................... 203/57, 60, 51, 56, 203/64, 18, 19, 14; 560/248, 234; 568/913, 918, 916

[56] References Cited

U.S. PATENT DOCUMENTS

| 1,770,414 | 7/1930 | Martin et al. | 560/234 |
| 2,489,619 | 11/1949 | Carlson et al. | 203/63 |
| 2,575,285 | 11/1951 | Carlson et al. | 203/63 |
| 4,379,028 | 4/1983 | Berg et al. | 203/60 |
| 4,469,905 | 9/1984 | Inwood et al. | 568/918 |
| 4,525,245 | 6/1985 | Berg et al. | 203/58 |

FOREIGN PATENT DOCUMENTS

| 1089744 | 9/1960 | Fed. Rep. of Germany | 203/64 |
| 46701 | 4/1979 | Japan | 560/248 |
| 967471 | 12/1960 | United Kingdom | 203/60 |

Primary Examiner—Wilbur Bascomb

[57] ABSTRACT n-Hexyl acetate cannot be completely removed from n-hexyl acetate- n-hexyl alcohol- water mixtures by distillation because of the presence of the minimum ternary azeotrope. n-Hexyl acetate can be readily removed from mixtures containing it, n-hexyl alcohol and water by using extractive distillation in which the extractive distillation agent is dimethylsulfoxide or a mixture of DMSO with a higher boiling organic compound. Typical examples of effective agents are DMSO; DMSO and tetraethylene glycol; DMSO, dimethylformamide and hexylene glycol.

2 Claims, No Drawings

SEPARATION OF N-HEXYL ACETATE FROM N-HEXYL ALCOHOL BY EXTRACTIVE DISTILLATION

This application is related to application Ser. No. 06/822,602 filed Jan. 27, 1986.

FIELD OF THE INVENTION

This invention relates to a method for separating n-hexyl acetate from n-hexyl alcohol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture n-hexyl acetate is by the catalytic esterification of n-hexyl alcohol with acetic acid. n-Hexyl acetate (b.p.=171.5° C.), n-hexyl alcohol (b.p.=157.5° C.) and water (b.p.=100° C.) form a minimum ternary azeotrope boiling at 97.0° C. and containing 18.5 weight percent n-hexyl acetate, 52.9 wt. % n-hexyl alcohol and 28.6 wt. % water. n-Hexyl acetate forms a binary azeotrope with water boiling at 97.4° C. and containing 39 wt. % n-hexyl acetate. n-Hexyl alcohol also forms a binary minimum azeotrope with water which boils at 97.8° C. and contains 25 wt. % n-hexyl alcohol. Thus in the esterification of n-hexyl alcohol with acetic acid to form n-hexyl acetate and water, the rectification of this mixture has two binary and a ternary azeotrope to content with, and yields the lowest boiling constituent, namely the n-hexyl acetate-n-hexyl alcohol-water ternary azeotrope. It is therefore impossible to produce n-hexyl acetate from n-hexyl alcohol and water mixtures by rectification because the lower boiling ternary azeotrop will always come off overhead as the initial product. Any mixture of n-hexyl acetate, n-hexyl alcohol and water subjected to rectification at one atmosphere pressure will produce an overhead product boiling at 97° C. and containing 18.5 wt. % n-hexyl acetate, 52.9 wt. % n-hexyl alcohol and 28.6 wt. % water. Extractive distillation would be an attractive method of effecting the separation of n-hexyl acetate from n-hexyl alcohol if agents can be found that (1) will break the n-hexyl acetate-n-hexyl alcohol-water azeotrope and (2) are easy to recover from the n-hexyl alcohol, that is, form no azeotrope with n-hexyl alcohol and boil sufficiently above n-hexyl alcohol to make the separation by rectification possible with only a few theoretical plates.

Extractive distillation typically requires the addition of an equal amount to twice as much extractive agent as the n-hexyl acetate-n-hexyl alcohol-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent by miscible with n-hexyl alcohol otherwise it will form a two-phase azeotrope with the n-hexyl alcohol in the recovery column and some other method of separation will have to be employed.

The breaking of this azeotrope by extractive distillation is a new concept. The closest applications of the concept might be the breaking of the methyl acetate-methanol azeotrope described by Berg & Yeh, CHEMICAL ENGINEERING COMMUNICATIONS, p.3219–3223, 1984, U.S. Pat. Nos. 4,543,164 and 4,549,938. Berg & Ratanapupech, U.S. Pat. No. 4,379,028 separated ethyl acetate from ethanol. Berg & Yeh, U.S. Pat. Nos. 4,507,176 and 4,525,245 separated n-butyl acetate from n-butanol.

TABLE 1

Effective Extractive Agents Containing Dimethylsulfoxide

| Compounds | Ratios | | Relative Volatilities | |
|---|---|---|---|---|
| Dimethylsulfoxide (DMSO) | 1 | 6/5 | 1.76 | 1.80 |
| DMSO, Ethylene glycol | $(\frac{1}{2})^2$ | $(3/5)^2$ | 1.80 | 1.82 |
| DMSO, Propylene glycol | " | " | 1.26 | — |
| DMSO, 1,3-Butanediol | " | " | 1.70 | 1.70 |
| DMSO, 1,4-Butanediol | " | " | 2.17 | 1.33 |
| DMSO, 1,5-Pentanediol | " | " | 1.70 | 1.56 |
| DMSO, Hexylene glycol | " | " | 1.12 | 1.25 |
| DMSO, 1,6-Hexanediol | " | " | 1.60 | 1.77 |
| DMSO, Triethylene glycol | " | " | 1.68 | 1.11 |
| DMSO, Tetraethylene glycol | " | " | 1.48 | 1.44 |
| DMSO, Dipropylene glycol | " | " | 1.24 | 1.45 |
| DMSO, Dimethylformamide (DMFA) | " | " | 1.46 | 1.75 |
| DMSO, DMFA, Ethylene glycol | $(\frac{1}{3})^3$ | $(2/5)^3$ | 1.30 | 1.37 |
| DMSO, DMFA, 1,3-Butanediol | " | " | 2.21 | 1.90 |
| DMSO, DMFA, 1,4-Butanediol | " | " | 1.57 | 1.75 |
| DMSO, DMFA, 1,5-Pentanediol | " | " | 1.41 | 1.65 |
| DMSO, DMFA, Hexylene glycol | " | " | 1.35 | 1.41 |
| DMSO, DMFA, Dipropylene glycol | " | " | 1.36 | 1.59 |
| DMSO, DMFA, Triethylene glycol | " | " | 1.22 | 1.28 |
| DMSO, DMFA, N,N—dimethylacetamide | " | " | 1.50 | 1.52 |

TABLE 1-continued
Effective Extractive Agents Containing Dimethylsulfoxide

| Compounds | Ratios | | Relative Volatilities | |
|---|---|---|---|---|
| DMSO, DMFA, 1,3-Butanediol, N,N—dimethylacetamide | " | " | 1.55 | 1.33 |

OBJECTIVE OF THE INVENTION

The object of this invention is to provide a process or method of extractive distillation that will enhance the relative volatililty of n-hexyl acetate from n-hexyl alcohol in their separation in a rectification column. It is a further object of this invention to identify suitable extractive distillation agents which will eliminate the n-hexyl acetate-n-hexyl alcohol-water ternary azeotrope and make possible the production of pure n-hexyl acetate and n-hexyl alcohol by rectification. It is a further object of this invention to identify organic compounds which in addition to the above constraints, are stable, can be separated from n-hexyl alcohol by rectification with relatively few theoretical plates and can be recycled to the extractive distillation column and reused with little decomposition.

SUMMARY OF THE INVENTION

The objects of the invention are provided by a process for separating n-hexyl acetate from n-hexyl alcohol which entails the use of dimethylsulfoxide, either alone or admixed with certain oxygenated or nitrogenous organic compounds.

DETAILED DESCRIPTION OF THE INVENTION

I have discovered that dimethylsulfoxide, either along or admixed with other organic compounds, will effectively negate the n-hexyl acetate-n-hexyl alcohol-water ternary azeotrope and permit the separation of pure n-hexyl acetate from n-hexyl alcohol by rectification when employed as the agent in extractive distillation. Table 1 lists dimethylsulfoxide (DMSO) and its mixtures and the approximate proportions that I have found to be effective. The data in Table 1 was obtained in a vapor-liquid equilibrium still. In each case, the starting material was the n-hexyl acetate-n-hexyl alcohol-water azeotrope. The ratios are the parts by weight of extractive agent used per part of n-hexyl acetate-n-hexyl alcohol-water azeotrope. The relative volatilities are listed for each of the two ratios employed. The compounds that are effective when used with DMSO are ethylene glycol, propylene glycol, 1,3-butanediol, 1,4-butanediol, 1,5-pentanediol, hexylene glycol, 1,6-hexanediol, triethylene glycol, tetraethylene glycol, dipropylene glycol, dimethylformamide and N,N-dimethylacetamide. The two relative volatilities shown in Table 1 correspond to the two different ratios investigated. For example, in Table 1, one part of DMSO with one part of the n-hexyl acetate-n-hexyl alcohol-water azeotrope gives a relative volatility of 1.76, 6/5 parts of DMSO give 1.80. One half part of DMSO mixed with one half part of ethylene glycol with one part of the n-hexyl acetate-n-hexyl alcohol-water azeotrope gives a relative volatility of 1.80, 3/5 parts of DMSO plus 3/5 parts of ethylene glycol gives 1.82. One third part of DMSO plus ⅓ part of dimethylformamide plus ⅓ part of 1,3-butanediol with one part of the n-hexyl acetate-n-hexyl alcohol-water azeotrope gives a relative volatility of 2.21, with 2/5 parts, these three give a relative volatility of 1.90. In every example in Table 1, the starting material is the n-hexyl acetate-n-hexyl alcohol-water azeotrope which possesses a relative volatility of 1.00.

TABLE 2
Data From Run Made In Rectification Column

| Agent | Wt. % n-Hexyl acetate | | Relative Volatility |
|---|---|---|---|
| | Overhead | Bottoms | |
| Dimethylsulfoxide | 72 | 15.5 | 1.795 |

Notes: Ternary mixture comprised 12.5% n-hexyl acetate, 57.5% n-hexyl alcohol, 30% water. Agent added at 20 ml/min. Reflux rate was 10–16 ml/min.

Dimethylsulfoxide (DMSO) whose relative volatility had been determined in the vapor-liquid equilibrium still, was then evaluated in a glass perforated plate rectification column possessing 4.5 theoretical plates. The n-hexyl acetate-n-hexyl alcohol-water mixture charged to the stillpot was 12.5% n-hexyl acetate, 57.5% n-hexyl alcohol and 30% water. The ratio of n-hexyl acetate to n-hexyl alcohol in the overhead is 2.57 which is greater than 0.35 and the results are presented in Table 2. Without the extractive agent, the overhead would approach the azeotrope whose ratio of n-hexyl acetate to n-hexyl alcohol is 0.35. This proves that the extractive agent is negating the azeotrope and makes the rectification proceed as if the azeotrope no longer existed and brings the more volatile components, n-hexyl acetate and water, out as overhead products. It is my belief that this is the first time that this has been accomplished for this azeotrope.

The data in Table 2 was obtained in the following manner. The charge was brought to boiling and after a half hour of operation in the 4.5 theoretical plate column to establish equilibrium throughout, DMSO at 95° C. and 10–16 ml/min. was pumped in. The rectification was continued for 1¼ hours with sampling of the overhead and bottoms after 75 minutes. The analysis is shown in Table 2 and was 72% n-hexyl acetate in the overhead and 15.5% n-hexyl acetate in the bottoms, both on a water-free basis, which gives a relative volatility of 1.795 of n-hexyl acetate to n-hexyl alcohol. This indicates that the ternary azeotrope has been negated and the separation accomplished. The n-hexyl acetate comes off in the form of its binary azeotrope with water which on condensation, immediately forms two layers. The solubility of n-hexyl acetate in liquid water is only 0.1%.

THE USEFULNESS OF THE INVENTION

The usefulness or utility of this invention can be demonstrated by referring to the data presented in Tables 1 and 2. All of the successful extractive distillation agents show that n-hexyl acetate, n-hexyl alcohol and water can be separated from their ternary azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity n-hexyl acetate from any mixture of these three including the ternary azeotrope. The stability of the compounds used and the boiling point difference is such that complete recovery and recycle is obtainable by a simple distillation and the amount required for make-up is small.

WORKING EXAMPLES

EXAMPLE 1

The n-hexyl acetate-n-hexyl alcohol-water azeotrope is 18.5 wt. % n hexyl acetate, 52.9 wt. % n-hexyl alcohol and 28.6 wt. % water. Fifty grams of the n-hexyl acetate-n-hexyl alcohol-water azeotrope and fifty grams of dimethylsulfoxide (DMSO) were charged to an Othmer type vapor-liquid equilibrium still and refluxed for 12 hours. Analysis of the vapor and liquid by gas chromatography gave a vapor composition of 34.2% n-hexyl acetate, 65.8% n-hexyl alcohol; a liquid composition of 22.8% n-hexyl acetate, 77.2% n-hexyl alcohol. This indicates a relative volatility of 1.76. Ten grams of DMSO were added and refluxing continued for another nine hours. Analysis indicated a vapor composition of 35.5% n-hexyl acetate, 64.5% n-hexyl alcohol, a liquid composition of 23.4% n-hexyl acetate, 76.6% n-hexyl alcohol which is a relative volatility of 1.80.

EXAMPLE 2

Fifty grams of the n-hexyl acetate-n-hexyl alcohol-water azeotrope, 25 grams of DMSO and 25 grams of tetraethylene glycol were charged to the vapor-liquid equilibrium still and refluxed for 12 hours. Analysis indicated a vapor composition of 32.1% n-hexyl acetate, 67.9% n-hexyl alcohol; a liquid composition of 24.4% n-hexyl acetate, 75.8% n-hexyl alcohol which is a relative volatility of 1.48. Five grams of DMSO and five grams of tetraethylene glycol were added and refluxing continued for another 12 hours. Analysis indicated a vapor composition of 31.7% n-hexyl acetate, 68.3% n-hexyl alcohol; a liquid composition of 24.3% n-hexyl acetate, 75.7% n-hexyl alcohol which is a relative volatility of 1.44.

EXAMPLE 3

Fifty grams of the n-hexyl acetate-n-hexyl alcohol-water azeotrope, 17 grams of DMSO, 17 grams of dimethylformamide and 17 grams of hexylene glycol were charged to the vapor-liquid equilibrium still and refluxed for eleven hours. Analysis indicated a vapor composition of 31% n-hexyl acetate, 69% n-hexyl alcohol; a liquid composition of 25% n-hexyl acetate, 75% n-hexyl alcohol which is a relative volatility of 1.35. Three grams each of DMSO, DMFA and hexylene glycol were added and refluxing continued for another 12 hours. Analysis indicated a vapor composition of 31.4% n-hexyl acetate, 68.6% n-hexyl alcohol; a liquid composition of 24.5% n-hexyl acetate, 75.5% n-hexyl alcohol which is a relative volatility of 1.41.

EXAMPLE 4

A glass perforated plate rectification column was calibrated with ethylbenzene and p-xylene which possesses a relative volatility of 1.06 and found to have 4.5 theoretical plates. A solution comprising 50 grams of n-hexyl acetate, 230 grams of n-hexyl alcohol and 120 grams of water was placed in the stillpot and heated. When refluxing began, an extractive agent consisting of pure DMSO was pumped into the column at a rate of 20 ml/min. The temperature of the extractive agent as it entered the column was 95° C. After establishing the feed rate of the extractive agent, the heat input to the n-hexyl acetate-n-hexyl alcohol-water in the stillpot was adjusted to give a total reflux rate of 10-16 ml/min. After 75 minutes of steady operation, the overhead and bottoms samples of approximately two ml. were collected and analysed using gas chromatography. The overhead analysis was 72% n-hexyl acetate, 28% n-hexyl alcohol. The bottoms analysis was 15.5% n-hexyl acetate, 84.5% n-hexyl alcohol. Using these compositions in the Fenske equation, with the number of theoretical plates in the column being 4.5, gave an average relative volatility of 1.795 for each theoretical plate.

The nature of the present invention having been described, what I wish to claim as new and useful and secure by Letters Patent is:

1. A method for recovering n-hexyl acetate from a mixture of n-hexyl acetate, n-hexyl alcohol and water which comprises distilling a mixture of n-hexyl acetate, n-hexyl alcohol and water in a rectification column in the presence of about one part of extractive agent per part of n-hexyl acetate-n-hexyl alcohol-water mixture, recovering n-hexyl acetate and water as overhead product and obtaining the n-hexyl alcohol and the extractive agent from the stillpot, the extractive agent comprises dimethylsulfoxide.

2. The method of claim 1 in which the extractive agent comprises a mixture of dimethylsulfoxide and at least one material from the group consisting of ethylene glycol, propylene glycol, 1,3-butanediol, 1,4-butanediol, 1,5-pentanediol, hexylene glycol, 1,6 hexanediol, triethylene glycol, tetraethylene glycol, dipropylene glycol, dimethylformamide and N,N-dimethylacetamide.

* * * * *